(12) United States Patent
Biber et al.

(10) Patent No.: US 11,119,164 B2
(45) Date of Patent: Sep. 14, 2021

(54) MAGNETIC RESONANCE FACILITY AND A METHOD FOR OPERATING A MAGNETIC RESONANCE FACILITY HAVING A PATIENT TABLE

(71) Applicant: Siemens Healthcare GmbH, Erlangen (DE)

(72) Inventors: Stephan Biber, Erlangen (DE); Lennart Kilian, Gauting (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/895,138

(22) Filed: Jun. 8, 2020

(65) Prior Publication Data
US 2020/0393527 A1    Dec. 17, 2020

(30) Foreign Application Priority Data
Jun. 13, 2019 (DE) .......................... 102019208612.8

(51) Int. Cl.
*G01R 33/30*    (2006.01)
*G01R 33/54*    (2006.01)
*A61B 5/055*    (2006.01)

(52) U.S. Cl.
CPC ............ *G01R 33/307* (2013.01); *A61B 5/055* (2013.01); *G01R 33/543* (2013.01)

(58) Field of Classification Search
CPC ...... G01R 33/307; G01R 33/543; A61B 5/704
See application file for complete search history.

(56) References Cited

U.S. PATENT DOCUMENTS

2010/0134315 A1*  6/2010  Teders .................. G08C 17/00
                                                          340/12.22
2014/0100675 A1   4/2014  Dold

FOREIGN PATENT DOCUMENTS

DE    102012003676 A1    8/2013
EP      2720094 A1       4/2014

OTHER PUBLICATIONS

German Office Action for German Application No. 10 2019 208 612.8 dated Mar. 25, 2020.

* cited by examiner

*Primary Examiner* — G. M. A Hyder
(74) *Attorney, Agent, or Firm* — Lempia Summerfield Katz LLC

(57) ABSTRACT

A method for operating a magnetic resonance facility is provided herein. The facility has a main magnet unit with a patient-receiving area, a movable, controllable patient table for positioning a patient in the patient-receiving area, a table control unit for controlling the patient table, and, on the main magnet unit, an operating facility that communicates with the table control unit, for operation of the patient table by a user. The operating facility has a first, electronic operating device for setting control parameters for a movement of the patient table to be performed, and a second, mechanical operating device for triggering the movement. In a safe operating mode, control parameters that have been set are communicated from the first operating device to the table control unit over a first communication channel, and a trigger signal, suitable for triggering the movement defined by the control parameters, is communicated from the second operating device, over two redundant second communication channels that are at least logically separated, to the table control unit, and processed separately there, wherein the movement is only triggered when there is a match between (Continued)

the trigger signal received over the two communication channels.

16 Claims, 3 Drawing Sheets

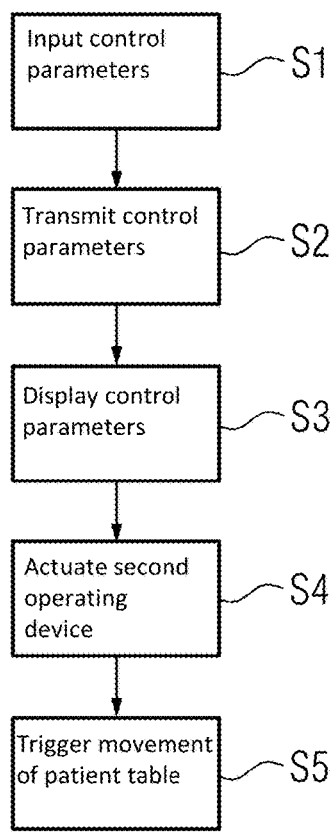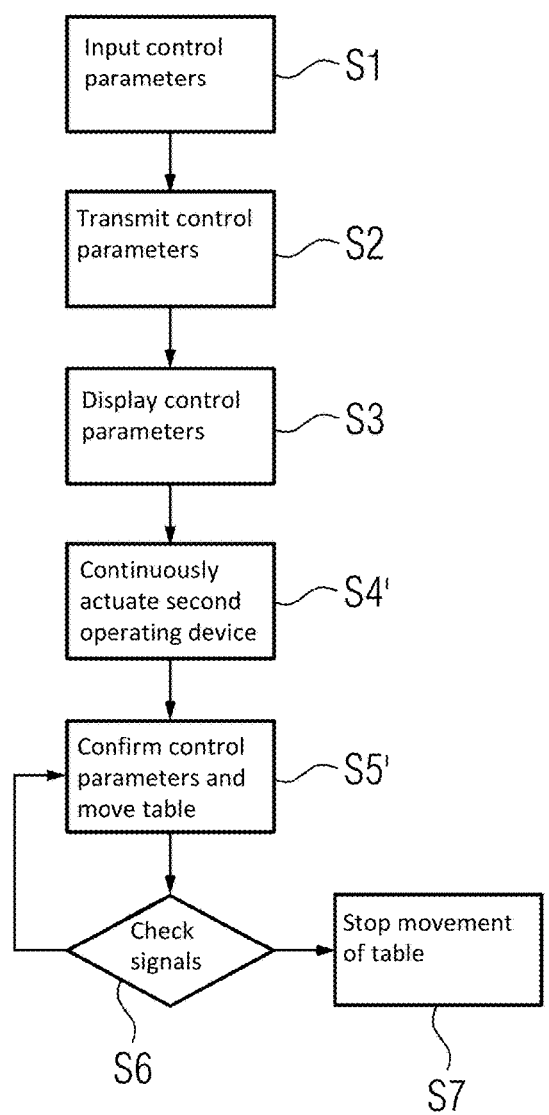

MAGNETIC RESONANCE FACILITY AND A METHOD FOR OPERATING A MAGNETIC RESONANCE FACILITY HAVING A PATIENT TABLE

The present patent document claims the benefit of German Patent Application No. 10 2019 208 612.8, filed Jun. 13, 2019, which is hereby incorporated by reference.

TECHNICAL FIELD

The disclosure relates to a method for operating a magnetic resonance facility that has a main magnet unit with a patient-receiving area, a movable, controllable patient table for positioning a patient in the patient-receiving area, a table control unit for controlling the patient table, and, on the main magnet unit, an operating facility that communicates with the table control unit, for operation of the patient table by a user. The disclosure also relates to a magnetic resonance facility.

BACKGROUND

Magnetic resonance imaging represents a well-established imaging modality in medical technology. Magnetic resonance facilities may have a main magnet unit within which, (e.g., in a cryostat or vacuum vessel), the superconducting main magnet is arranged for the purpose of generating the basic magnetic field of the magnetic resonance facility, nuclear spin being oriented within this basic magnetic field. The main magnet unit has a cylindrical patient-receiving area into which, by a patient table, a patient may be put and in which the patient may be positioned in relation to the receiving area such that the patient is located inside the homogeneous space, that is to say the imaging space, of the magnetic resonance facility.

For operation of the patient table, the prior art has already proposed, for example, control buttons and/or a jog wheel on the casing of the main magnet unit. As an alternative, there have also been proposals to provide a touch screen on the casing of the main magnet unit such that components of the magnetic resonance facility, and in particular also of the patient table, may be operated on site.

It has also already been proposed that, similarly to other modalities such as computed tomography or fluoroscopy, magnetic resonance imaging should be used during surgery, for example, to monitor the progress of a procedure. Examples of such procedures, (e.g., minimally invasive procedures), include procedures using needles, cardiac catheter ablations, (e.g., with access through the femoral artery), and other procedures in which medical devices or instruments are introduced into a patient's body.

The use of magnetic resonance imaging in this context requires the patient to be moved out of and into or within the patient-receiving area (e.g., also called the tunnel). This entails certain risks, because the patient-receiving area may be extremely small, (e.g., having a diameter of 60 to 70 cm). In that case, it is possible for medical devices and/or instruments to collide with the inner wall of the patient-receiving area or with other components. Another problem may be when cables, hoses, and/or catheters become caught, which may result in their undesired movement. This entails risks for the patient that should be avoided to the greatest possible extent.

It has thus been proposed in the prior art that the magnetic resonance facility be provided on the main magnet unit and/or at another position, where appropriate also held in the hand, with an emergency stop button that halts and prevents any movement of the patient table as quickly as possible. However, the consequence of this is reliance on the attentiveness and reaction time of a user, which may lead to problems, in particular, if the patient table is moving relatively quickly.

SUMMARY AND DESCRIPTION

The object of the disclosure is therefore to provide a way of operating the patient table of the magnetic resonance facility that is better from the point of view of safety of use of the patient table, in particular during procedures involving magnetic resonance image monitoring of a patient.

This object is achieved by a method and a magnetic resonance facility disclosed herein. The scope of the present disclosure is defined solely by the appended claims and is not affected to any degree by the statements within this summary. The present embodiments may obviate one or more of the drawbacks or limitations in the related art.

In one exemplary method, the operating facility has a first, electronic operating device, for setting control parameters for a movement of the patient table to be performed, and a second, mechanical operating device for triggering the movement. In a safe operating mode, control parameters that have been set are communicated from the first operating device to the table control unit over a first communication channel. Additionally, in the safe operating mode, a trigger signal, suitable for triggering the movement defined by the control parameters, is communicated from the second operating device, over two redundant second communication channels that are at least logically separated, to the table control unit, and processed separately there, wherein the movement is only triggered when there is a match between the trigger signal received over the two communication channels.

Thus, an operating concept is proposed which an electronic first operating device, (e.g., a touch screen), is used for definition by a user of control parameters that are to be used for movement for the patient table. The first operating device uses a comparatively insecure communication channel with the table control unit, which is supplemented by a second, (e.g., mechanical) operating device (that is to say a triggering operating device such as a button) that communicates with the table control unit over a two logically separated communication channels (e.g., a communication path that is made comparatively secure by redundancy).

The first operating device, which has a display apparatus for the supported setting of the control parameters in a manner as simple as possible, may be a touch screen that is arranged on a casing of the main magnet unit and allows control parameters to be set simply and intuitively. As an alternative, it is also possible for other operating devices with display apparatuses to be used, e.g., a screen with associated keyboard. While the second operating device may be arranged on the main magnet unit, it is also conceivable, in relation to the first operating device, to provide this remotely from the main magnet unit, where appropriate to provide it outside the shielded space, for example as a keyboard and/or mouse of a host computer. The first operating device may be a touch screen, but adjacent to the second operating device on the main magnet unit.

The second operating device may be a trigger button, which may also be part of a jog shuttle or jog wheel or similar. It is also possible, when not in the safe operating mode, for the second, mechanical operating device to be used by itself for directly triggering movement processes, as is in principle already known from the prior art, in particular for jog wheels and similar.

The first and second communication channels are favorably at least partly also separated physically, wherein the logical separation of the second communication channels and the consequent separate generation before sending, and the processing on receipt, of the trigger signals represents the contribution to safety. The at least partial use of the same communication line, in particular the same communication cable, reduces the complexity (in certain cases already considerable) of cabling on the magnetic resonance facility.

The trigger signal of the two second communication channels may be generated by its own switch, actuated mechanically by the second operating device, and/or the logical separation of the second communication channels may be created at least by the use of two different communication protocols, e.g., CANopen and CANsafe. Thus, for triggering, it is necessary to actuate both switches, which independently generate a trigger signal which is then encoded, (e.g., independently and in different ways depending on the communication protocol), and communicated to the table control unit, (e.g., by a CAN bus). Because different communication protocols are used for the trigger signals, these are also separated, so are received and decoded in the table control unit by different electronic receiving units. Thus, the maximum possible logical separation is achieved, enabling the greatest possible redundancy and thus safety of triggering.

The table control unit may form a component that is secure, (e.g., safety measures are also taken within the table control unit that to the greatest possible extent prevent erroneous control of the patient table). A focus of this disclosure is on implementing a safe operating concept, however. The table control unit controls and monitors, e.g., the patient table, in particular as regards to the position and speed of the patient table. In particular, it is thus in communicative connection with movement actuators and/or sensors of the patient table.

Input of the control parameters, (e.g., the type of movement), and the actual triggering of the movement are performed by way of physically separated operating device and at least partly physically and logically separated communication paths. The first operating device communicates over the first communication channel, which (e.g., in the case of a touch screen), may utilize in part a proprietary or commercially available HMI protocol together with the table control unit, in order to communicate the movement parameters and to prepare them for the imminent arrival of a movement request (e.g., in the form of the trigger signals). The movement, (e.g., approach to a target), is triggered by the second operating device, (e.g., actuation of a button), in particular within a predefined confirmation period after the control parameters have been transmitted. The corresponding communication path is made redundant by the use of two second communication channels, in particular as regards switches as physically separated generation devices (e.g., logical dual-channel construction). The table control unit only starts the movement when two start commands (matching trigger signals) are received. Thus, a safe path is produced for triggering and stopping the movement, and a less safe path is produced for initializing and parameterizing the movement by way of visual first, and in particular touch device or operating device (input devices). Incorporation of the less safe path for setting the movement parameters enables additional safety, in that movement by way of the second operating device is only triggered when a movement has already been initialized by way of the first operating device. In other words, the table control unit only triggers a movement when it has also already received control parameters parameterizing the movement.

Here, it may favorably be provided for the control parameters to include an axis of movement, a direction of movement, a target position, a movement distance, a speed of movement of the patient table, a mode of movement, or a combination thereof. A mode of movement may define whether travel is to be continuous (discussed in greater detail below) or an approach to a target. In concrete terms, the axis of movement (including direction), the speed, a target position, an operating mode, or a combination thereof may be transmitted as control parameters. It goes without saying that other control parameters may also be used.

The table control unit may use the control parameters at least in part as limits. This is because, in the final analysis, the control parameters specify which limits are never to be exceeded, (e.g., as regards speed and target position). For example, if a table speed defined by the control parameters is exceeded by the current speed of the patient table and/or if a target position defined by the control parameters is overshot by the current position of the patient table, the table control unit brings the patient table to a safe standstill position, in particular within a maximum stopping time. However, it is also conceivable to plan anticipatory braking actions within the table control unit.

In a particular development, after the table control unit has received the control parameters, the table control unit transmits the control parameters back over the first and/or at least one further communication channel to the first operating device. The control parameters that have been transmitted back are displayed to a user on a display apparatus of the first operating device. In this way, for the purpose of further enhancing safety, the user may check the control parameters and then confirm by the second operating device that the control parameters the user wanted have indeed arrived at the table control unit, because it is not the control parameters in the second operating device that are displayed after input but the control parameters that are transmitted back by the table control unit and interpreted there as a movement request for the purpose of preparing an imminent movement. In other words, in this embodiment, it is possible to provide that the control parameters in the table control unit are correct, by "mirroring" them back. The user checks whether the displayed control parameters correctly reproduce the movement that the user wants, and only then provides confirmation, by the second operating device and the redundant trigger signal, or, in an intermediate act, by the first operating device.

In this embodiment, an architecture for functionally reliable movement of the patient table is provided with minimal complexity of hardware and software, built on four pillars: (1) a first operating path with a comparatively insecure first communication channel to the table control unit, a first electronic operating device, (e.g., a touch screen), and where appropriate computers for requesting and parameterizing the movement; (2) a confirmation by the user that the control parameters that have been input, transmitted, transmitted back, and displayed are correct; (3) a second operating path with a comparatively secure communication path including two second communication channels, and a second operating device for triggering movement; and (4) a communication architecture that, by querying back and clearing the sequence and hierarchy of the movement definition and triggering of movement, provides that an insecure condition does not arise.

As already mentioned, it is conceivable to interpret actuation of the second operating device as confirmation of the displayed, transmitted-back control parameters, with the result that there is no need for an operational action in relation to a separate confirmation. Here, the trigger signal thus serves as a confirmation signal. However, also conceivable is an embodiment that slightly enhances safety, in which on detection of an actuation of the first operating device over the first communication channel, which confirms the transmitted-back control parameters, a confirmation signal is sent to the control unit, wherein the presence of the confirmation signal is used as an additional condition for triggering the movement defined by the control parameters. For example, a confirmation operating pane on a touch screen may be displayed as the first operating device, wherein the confirmation is sent when the touch screen is touched. Only once the control parameters have been confirmed is it possible to trigger movement by way of the second operating device.

Another favorable development in this context provides for received control parameters to undergo an error check at the operating facility and/or table control unit, and if an error is detected by the table control unit an error signal is sent to the first operating device over the first and/or the further communication signal. For example, an error check of this kind may include the detection of control parameters that lie outside the technical possibilities available to the movement actuators of the patient table and/or that exceed limits predetermined for the safe operating mode, or movement parameters derived from these, and, if they are present, the generation of an error signal. If, for example, there is a connection to a system that manages workflow, then workflow data may also be evaluated to check whether the control parameters are meaningful in the context of the current treatment step for a patient. For example, in this way, an erroneous direction of movement may be detected, if the patient has already been put into the patient-receiving area and, for the next treatment step in the workflow, should be moved out of the receiving area, but the control parameters indicate moving the patient further into the receiving area. In this way, it is possible to further enhance safety overall. For this purpose, an error that is identified during checking is displayed on the display apparatus of the first operating device. An error signal may also contain, as error information, a suggestion on correction, which is likewise displayed.

In one development, it may be provided for the first communication path to include at least one further processing facility, in which the control parameters are converted to a communication protocol that is suitable for the table control unit, in particular, a communication protocol that is also used for the second communication path and/or that uses the same communication line to the table control unit. Many control architectures that are already known for magnetic resonance facilities have further control and/or processing units in any case, (e.g., a central control computer), which may lie on the communication path that provides the first communication channel. This makes it possible, in particular, also to operate and/or adjust other components of the magnetic resonance facility by way of the first electronic operating device, (e.g., the touch screen), and/or to move part of control of the first operating device to another location. If the first operating device uses, for example, an HMI protocol that is particularly configured for optical signal transmission, it may be favorable to provide, on the first communication channel to the table control unit, a processing facility that converts the control parameters from the HMI protocol that is first used into a further communication protocol suitable for the table control unit. For example, the communication protocol that is suitable for the table control unit may be a communication protocol that is also used on one of the second communication channels, (e.g., CANopen). In this way, it is in particular also possible to at least partly use the same communication line before the table control unit is reached in order to reduce the complexity of cabling. For example, the communication line may be a CAN bus on which the control parameters are communicated according to the CANopen protocol, and the trigger signals are each likewise communicated by the CANopen and moreover the CANsafe protocol. The processing facility may be the central control computer or a component of the control computer. However, it is also conceivable to provide an additional processing facility as a type of interface. Overall, the procedure is incorporated into an already existing architecture in optimum manner.

In addition to changing protocols, the interposed further processing facility may also serve for other purposes. For example, it may be provided for control parameters that are input through the further processing facility to be converted into a format suitable for control in the table control unit such that they are interpreted directly in the table control unit, and values that are intuitively comprehensible to the user may be used at the first operating device.

In the context of the present disclosure, it is not only favorable to clearly define sequences in the proper order, so that safe operation of the patient table is provided in the safe operating mode, but additionally it may be extremely advantageous to enhance safety by defining suitable time windows for actions and signals, (e.g., to provide control parameters with a duration of validity and/or a tolerance time window for signals). This may also be used to implement continuous travel, (e.g., by holding down the second operating device).

It may thus be provided, for the purpose of implementing continuous travel by continuously actuating the second operating device, for the table control unit to be constructed for stopping movement of the patient table unless both trigger signals are received within a predefined continuous period. If an operating variant of this kind is to be implemented in the safe operating mode, and in this respect also a high level of safety is to be provided, it is possible at any time to query whether the two trigger signals actually match. In this case, it may be provided for example for the length of the continuous period to be in a range of 20 to 200 milliseconds (ms), (e.g., 100 ms).

In concrete terms, the sending units of the second operating device, in which the trigger signals are generated, may in this case be constructed for the purpose of generating trigger signals if the second operating device is continuously actuated at a frequency whereof the period is less than or equal to the length of the continuous period. For example, it may thus be provided for trigger signals to be generated every 100 ms while the second operating device is actuated. If even one of the two redundant trigger signals is missing during a time step, the patient table is halted immediately.

In a further advantageous embodiment of the method, it may be provided for the operating facility to be constructed for sending the trigger signals only when the second operating device is actuated within a confirmation period after the control parameters have been sent and/or, as an additional condition for triggering the movement, for the table control unit to monitor whether the matching trigger signals have been received within the confirmation period after the control parameters have been received. The confirmation period may last for 2 to 30 seconds, (e.g., 15 seconds). The confirmation period is therefore a kind of duration of validity for a movement request defined by control parameters that have been sent to the table control unit. In other words, the confirmation period sets a limit that determines how long the system will accept subsequent trigger signals (e.g., movement confirmations). Once the confirmation period has expired, actuations of the second operating device have no further effect. Here, the confirmation period may be monitored within the operating facility itself. It is also possible to monitor the confirmation period within the table control unit, e.g., starting with receipt of the control parameters. In this way, for the purpose of enhancing safety, ultimately a time-based relationship is established between input and sending of the control parameters and the subsequent confirmation by way of the second operating device.

A further favorable embodiment provides, for the purpose of generating the trigger signals in the second operating device and/or for checking the validity of the detection of two trigger signals received by the table control unit, for a check to be made of whether the actuation of the second operating device takes place for at least a purposefulness period. Favorably, the purposefulness period may last for 0.1 to 2 seconds, (e.g., 1 second). The purposefulness period thus provides a barrier to triggering a movement of the patient table as a result of unintentionally and briefly actuating the second operating device, (e.g., a trigger button). If, for example, a user inadvertently touches the second operating device with their shoulder, and this contact and hence the inadvertent actuation is shorter than the length of the purposefulness period, then no trigger signals are generated.

Favorably, because of the additionally required operational actions, the safe use of the patient table that is described above is only performed if the level of safety required is indeed this high. The result is that, in addition to the safe operating mode, it is also possible for a normal operating mode to exist, (e.g., one in which movement of the patient table may be requested solely by way of the second operating device). For example, whenever critical situations are expected during imaging, it is possible to activate the safe operating mode on the magnetic resonance facility, (e.g., for procedures that are particularly minimally invasive for the patient). Otherwise, for example, during routine imaging, the normal operating mode may be used, because the risks are then significantly smaller. A safe procedure should likewise be provided for deactivating the safe operating mode, such that the possibility of inadvertent deactivation may be substantially ruled out.

Accordingly, for the purpose of deactivating the safe operating mode and switching to a normal operating mode in which the patient table may be moved solely by way of the second operating device, a development of the present disclosure provides for a challenge-response method to be used between the table control unit and the operating facility, or for there to be a check for actuation of the second operating device taking place in particular within the confirmation period after deactivation has been selected by the first operating device. Thus, for example, if a user requests deactivation of the safe operating mode by way of the operating facility, the operating facility may transmit a corresponding query signal to the table control unit. When the table control unit receives this query signal, the table control unit may select a challenge and send a corresponding answer message to the operating facility, wherein the challenge may require user interaction. Examples of such challenges include so-called Captchas and/or images with numbers to be read by the user. The user replies to the corresponding challenge at the operating facility, in particular the first operating device, and the corresponding response is sent to the table control unit as a response message. The table control unit then checks whether the response correctly matches the challenge, and if there is a match it deactivates the safe operating mode.

In another variant, it may also be provided for the query signal to be sent to the table control unit if a deactivation operating element is selected at the first operating device. Only if an actuation of the second operating device is carried out within a deactivation period, (which may advantageously correspond to the confirmation period, and corresponding matching trigger signals are received by the table control unit), is the safe operating mode actually deactivated. For example, it is thus possible, if a touch screen is used, for a corresponding operating panel for deactivation of the safe operating mode to be provided on the touch screen. When the touch screen is actuated for the request signal to be sent to the table control unit and a corresponding indication to be output to the touch screen, confirmation is required by the second operating device within the deactivation period.

Favorably, activation and/or non-activation of the safe operating mode may be displayed by a display the operating facility, (e.g., by backlighting the second operating device and/or by a corresponding mechanical switching of the second operating device). In this way, the user is always informed whether the safe operating mode is active or not and consequently how the patient table has to be operated. For example, a light effect, (e.g., using a light emitting diode), may be used in the second operating device or around the borders thereof, with the result that the safe condition of the system is displayed. Here, display at the second operating device may be provided, in particular if in normal operating mode this is the principal or sole point of operating the patient table. It is also possible for display to be performed by a predefined mechanical switching of the second operating device.

As well as the method, the disclosure also relates to a magnetic resonance facility that has a main magnet unit with a patient-receiving area. The magnetic resonance facility also includes a movable, controllable patient table for positioning a patient in the patient-receiving area. The magnetic resonance facility also includes a control facility that is constructed in particular for performing a method as claimed in one of the preceding claims, with a table control unit for controlling the patient table. The magnetic resonance facility also includes an operating facility on the main magnet unit, wherein the operating facility communicates with the table control unit by way of a communication facility, for operation of the patient table by a user. The operating facility has a first, electronic operating device for setting control parameters for a movement of the patient table to be performed. The operating facility also has a second, mechanical operating device for triggering the movement. The communication facility has a first communication channel for communicating control parameters that have been set to the table control unit in a safe operating mode and at least two redundant second communication channels that are at least logically separated, for communicating to the table control unit a respective trigger signal when the second operating device is actuated. Further, the table control unit has two physically separated receiving units for the trigger signals and is constructed for triggering a movement defined by the control parameters only when there is a match between the trigger signals received.

All the embodiments relating to the method may be transferred analogously to the magnetic resonance facility, by which the advantages mentioned above may thus likewise be obtained.

BRIEF DESCRIPTION OF THE DRAWINGS

Further advantages and details of the present disclosure are apparent from the exemplary embodiments described below and on referring to the drawing, in which:

FIG. 4 depicts an example of how movement to a target position is controlled.

FIG. 5 depicts an example of how continuous movement is controlled.

DETAILED DESCRIPTION

Figure 1:
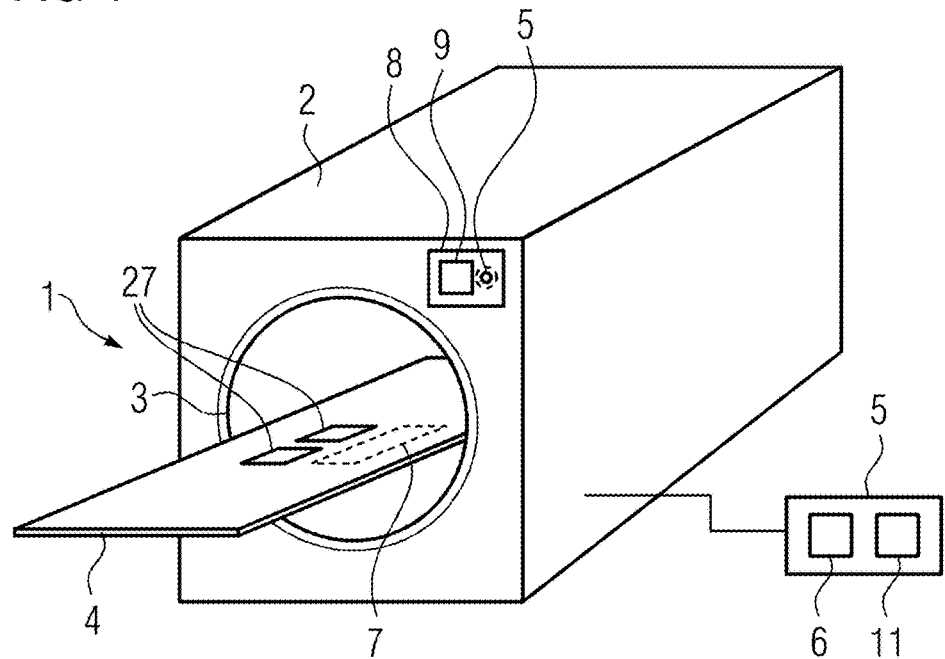
FIG. 1 depicts a sketch of the principle of a magnetic resonance facility according to an embodiment.

FIG. 1 depicts a sketch of the principle of a magnetic resonance facility 1. The magnetic resonance facility 1 includes a main magnet unit 2 in which there is defined a patient-receiving area 3 into which a patient may be put by a patient table 4. The magnetic resonance facility 1 further includes a control facility 5, which controls the operation of various components of the magnetic resonance facility 1 and in particular also has a table control unit 6, which controls actuators 7 for moving the patient table 4 and may receive information from sensors 27 of the patient table 4. The control facility 5, (wherein some of the components may be arranged in the main magnet unit 2 but some of the components may be arranged in a room outside the shielded space), further has an operating facility 8. The operating facility 8 has, arranged on a front side on the casing of the main magnet unit 2, a first operating device 9, (e.g., a touch screen), and a second operating device 10, (e.g., a trigger button or a jog wheel), as a mechanical operating device. Because operation of the patient table 4 is also to be performed by way of the operating facility 8, the control facility 5 also has a communication facility 11, which provides communication channels for communication between the table control unit 6 and the operating facility 8. The control facility 5 is constructed for carrying out the method.

Figure 2:
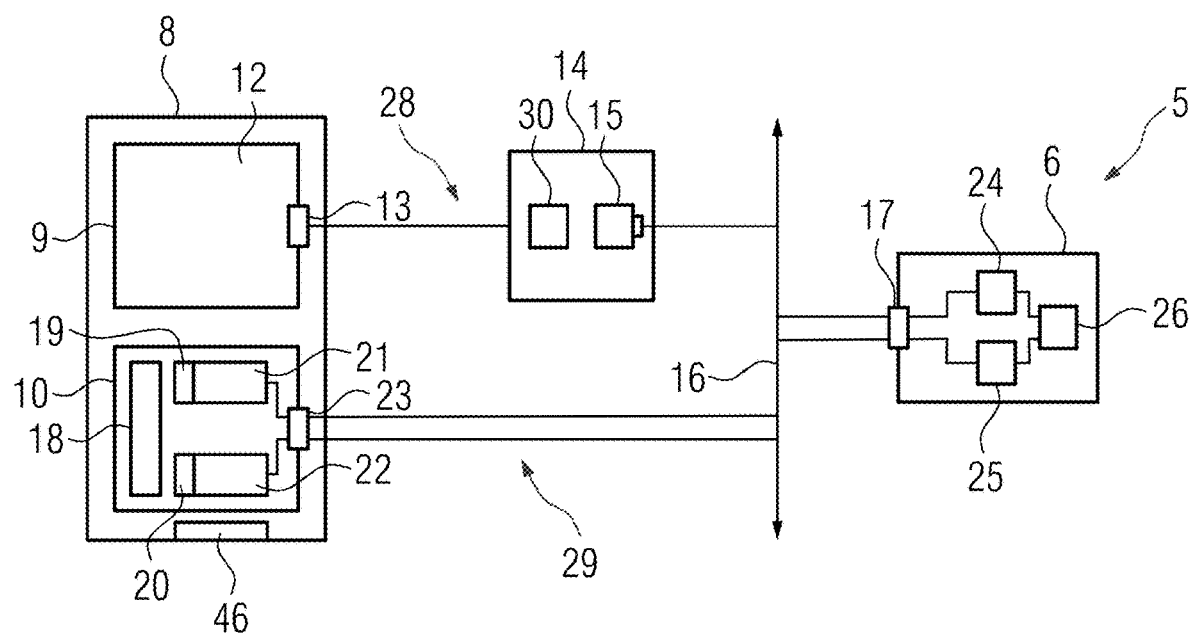
FIG. 2 depicts an example of functional components of the control facility of the magnetic resonance facility.

In this respect, FIG. 2 shows the construction of the control facility 5 in somewhat more detail. As explained above, the operating facility 8 has a touch screen 12 as the first operating device 9, which communicates over an interface 13 by an HMI protocol in the present case with a central control computer 14, as or including at least one second processing facility. The control computer 14 in turn has a coding unit 15 in order to pass information—or in concrete terms, control parameters for the patient table 4—by the CANopen protocol to a CAN bus 16 to which the table control unit 6 is also attached. The latter accordingly has a CAN interface 17.

Further, the operating facility 8 includes the second operating device 10, which in the present case has a mechanical trigger button or operating button 18. If the mechanical operating button 18 is pressed by a user, then, if operation is correct, the second operating device 10 actuates two separate mechanical switches 19, 20, each of which is coupled to a sending unit 21, 22. If the corresponding switch 19, 20 is actuated at least for a purposefulness period, the sending units 21, 22 each generate trigger signals suitable for the CAN bus 16, wherein the sending unit 21 uses the CANopen protocol and the sending unit 22 uses the CANsafe protocol. Trigger signals that are accordingly generated are passed over a CAN interface 23 to the CAN bus 16. There are separated receiving units 24, 25, respectively, for CANsafe and CANopen in the table control unit 6, with the result that the two different, redundant trigger signals are decoded separately and are accordingly passed on to a controller 26, which may include an encoder for information from the sensors 27 of the patient table 4 and/or a motor driver for the movement actuators 7 of the patient table 4. In each case, the controller 26 implements a logic that is described in more detail below.

Regarding the patient table 4 and its operation, the table control unit 6 or the control facility 5 may be operated in two modes, similar to a normal operating mode in which operation of the patient table 4 may be achieved by way of the second operating device 10 alone, and a safe operating mode in which operation of the patient table is only possible in a secure manner, using both the first operating device 9 and the second operating device 10.

Here, the safe operating mode is used in particular when carrying out in particular minimally invasive procedures on a patient on the magnetic resonance facility 1, in which case for example medical instruments project out of the patient and/or further devices/cabling are arranged in the region of the patient. In that case, the patient table 4 has to be moved with the utmost caution. In the operating concept described below, a first communication channel 28 and two second, logically separated communication channels 29 are used. The first communication channel 28, which has implicitly already been described in relation to FIG. 2, connects the first operating device 9 to the table control unit 6 and may be used to communicate to the table control unit 6 control parameters for the patient table 4 that have been input by the first operating device 9, or to communicate control parameters received there back to the first operating device 9. Control parameters for the patient table may include an axis of movement, a direction of movement, a target position, a movement distance, a speed of movement of the patient table, a mode of movement such as continuous travel, approach to a target, or combinations thereof.

Control parameters that are input at the first operating device 9 are first transmitted by an in particular proprietary HMI protocol, tuned to optical signal transmission, to the control computer 14, wherein different types of communication may be used between components of this control computer 14, (e.g., an Ethernet). Optionally, the control computer 14 may include a conversion unit 30, in which the input control parameters are converted to control parameters that are suitable for use for controlling the table control unit 6. The conversion unit 15 converts the control parameters for transmission by the CANopen protocol, and these are transmitted to the table control unit 6.

Although the two second communication channels 29 use the same communication line, (e.g., the CAN bus 16), the channels are logically separated, because the trigger signals are generated separately and are transmitted using different protocols, (e.g., CANopen and CANsafe). Once the trigger signals have been received, the trigger signals are also processed separately by the receiving units 24, 25. As a result of this redundancy, the second communication path formed by the second communication channels 29 is considered more secure than the first communication path formed by the first communication channel 28.

In addition to the exemplary embodiment described here, a physically separated implementation of the second communication channels 29 or indeed of the first and second communication paths in their entirety is also possible. Additionally, other communication protocols may also be used.

Figure 3:
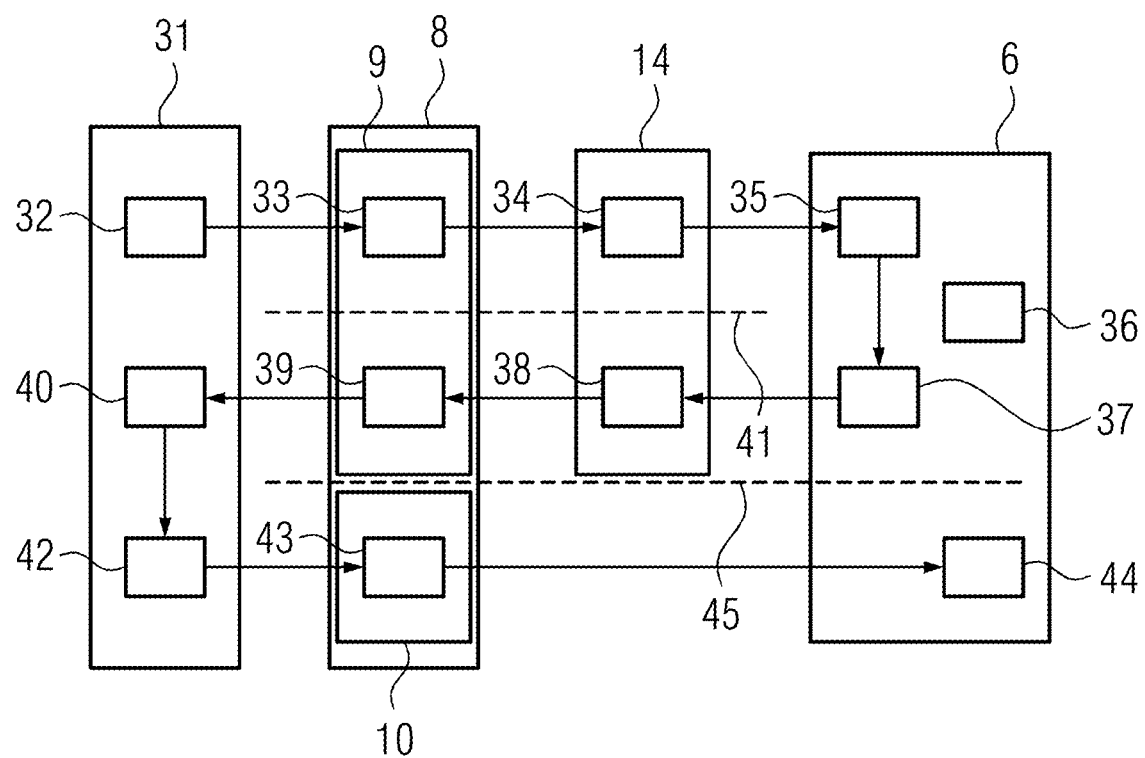
FIG. 3 depicts an example of a sequence for controlling movement of a patient table of the magnetic resonance facility.

FIG. 3 shows the operating concept implemented by the control facility 5 using the architecture of FIG. 2, in the safe operating mode. Here, acts shown within the box 31 indicate actions to be performed by the user.

Operation of the patient table 4 begins at act 32, in that a user operating the equipment considers suitable control parameters for the movement of the patient table 4 to be performed. In act 33, the control parameters are received by the operating facility 8 on a user interface and displayed on the touch screen 12. The control parameters that are input—with a first check for consistency already being possible, at the operating facility 8 or at the control computer 14 which fulfills this task—are then communicated to the table control unit 6 over the first communication channel 28, wherein, as already described, a conversion may optionally be performed at the control computer 14 in act 34 for the purpose of making them directly usable by the table control unit 6.

In act 35, the control parameters are received at the table control unit 6, which, because the table control unit is in the safe operating mode, initially interprets the control parameters only as a request for movement, and sets the control parameters in a preparatory manner for a future movement. Here, according to act 36, an error check of the received control parameters is also performed so that errors and inconsistencies may be identified, for example, in relation to a known current workflow act or the technical possibilities for the patient table 4 or its actuators 7. In the event of errors, an error signal may be generated, where appropriate also with a proposal for correction. The error signal may be transmitted back to the operating facility 8 for display.

In act 35, the control parameters are in particular interpreted as limits in order for example to plan or control a safe movement sequence within the limits defined by the control parameters.

In act 37, the control parameters that have been received are recoded and, by way of the control computer 14, optionally with re-conversion in act 38, are transmitted back to the operating facility 8. There, the transmitted-back control parameters are displayed by the touch screen 12 as the display apparatus, in act 39. Thus, in act 40, the user may check whether the correct control parameters have been set in a preparatory manner in the table control unit 6. If the error check in act 36 has identified and corrected errors, the corrections may be marked accordingly on the control parameters in the display. Overall, this is a kind of mirroring back that already significantly enhances safety.

In particular, this mirroring back already provides a functional autonomy barrier 41, likewise indicated in FIG. 3, because neither the control computer 14 nor the touch screen 12 is able to provide consistent original and back-transmitting control parameters that were inconsistent to start with.

In act 42, provided the user finds that the displayed control parameters are correct, the user may decide to trigger movement. In other words, if the desired and back-transmitted displayed control parameters consistently define the desired movement, then in order to start movement the user actuates the second operating device 10, or in concrete terms the operating button 18. This actuation is received by the operating facility 8 in act 43, and the redundant trigger signals are generated, as already described in relation to FIG. 2, and sent with logical separation over the corresponding second communication channels 29 to the table control unit 6, where they are received in act 44. Only if the two trigger signals match is the movement according to the control parameters triggered and is the patient table moved as a result of corresponding control by the movement actuators 7.

As a result of using the different operating device and the different communication paths, a technical autonomy barrier 45 is created, because there is technical autonomy between the first operating device 9 and the second operating device 10. Safety is further enhanced by the dual-channel architecture, resulting in the security of a single-fault condition.

In the safe operating mode, therefore, a certain secured action sequence is required in order for movement of the patient table 4 to be achieved. At the same time, for further enhancement of safety, certain periods are also defined in order to establish a time-based relationship between actions.

It should be noted that in act 43 the trigger signals are only generated if the second operating device 9 has been actuated at least for a purposefulness period, (e.g., one second). In this way, brief inadvertent contacts/actuations of the second operating device 10 cannot result in an undesired triggering of movement of the patient table 4. Further, a confirmation period, (e.g., 15 seconds), is defined, wherein after the control parameters have been received by the table control unit 6, the matching trigger signals arrives at the table control unit 6 within this confirmation period, with the result that a time-based relationship between the movement request and the actual triggering of movement is required. Trigger signals that arrive after the confirmation period has expired no longer result in triggering of movement of the patient table 4.

FIG. 4 shows a sequence for an approach to target by the patient table 4 (e.g., for automatically moving the patient table 4 to a target position simply by actuating the second operating device 10). In act S1, the appropriate control parameters, which include the information that approach to a target position is to be performed, are input by the first operating device 9 and are transmitted to the table control unit 6 over the first communication channel 28 in act S2. After an optional error check there, the control parameters are transmitted back to the first operating device 9 over the first communication channel 28 in act S3 and are there displayed to the user, who may check them. If the user decides that they are correct, he or she actuates the second operating device 10 in act S4, with the result that the trigger signals are generated with the correct function and transmitted to the table control unit 6 over the newly separated second communication channels 29.

In act S5, the table control unit 6 triggers movement of the patient table 4 according to the control parameters specifically if matching trigger signals have been received within the confirmation period. In that case, the patient table is moved by the movement actuators 7 until it has reached the requested target position.

FIG. 5 shows the case of requesting continuous movement. Here, there are no changes to acts S1 to S3 apart from the fact that no target position is produced as the control parameter, but rather the control parameters define the fact that continuous movement of the patient table 4 is desired.

Accordingly, in act S4' the user continuously actuates the second operating device 10 for as long as the user desires movement of the patient table 4. As long as the second operating device 10 is actuated, and after the desired purposefulness period has expired, the sending units 21, 22 each emit a respective first and second trigger signal, periodically at an interval of 100 ms. If, in act S5', the two matching trigger signals are received, this is considered to be a confirmation of the control parameters, and movement of the patient table 4 is started in the direction of movement defined by the control parameters. However, in act S6, a check is then made of whether the next two matching trigger signals have been received within a continuous period, in the present case for example 120 ms, because they are after all emitted periodically at an interval of 100 ms. If even one of these trigger signals is absent, then, in act S7, movement of the patient table 4 is halted immediately. Otherwise, it is continued in accordance with act S5'.

The confirmation period is monitored in act S5' as well. A continuation of the corresponding movement is also possible in that, in act S7, the confirmation period is started again, with the result that if, (e.g., within 15 seconds), the second operating device 10 is once more continuously actuated, further movement of the patient table 4 may be triggered again.

In this way, an insecure initialization path with computers and touch screen 12 for requesting and parameterizing the desired movement of the patient table 4 is thus combined with a secure trigger path for triggering movement and where necessary for stopping movement, to start movement going. As a result of the "mirroring back" of control parameters, safety is further enhanced, while moreover there is a communication architecture that, as a result of querying back and clearance, defines the sequence and hierarchy of triggering movement such that unsafe conditions are avoided.

In the exemplary embodiment described here, there is also protection against deactivation of the safe operating mode. For this, there are substantially two possibilities. The first possibility uses an operating element/operating panel displayed on the touch screen, wherein on actuation thereof a request signal is sent to the table control unit 6. When this is received, a challenge is selected that is processed by the user and sent back to the operating facility 8, or the touch screen 12. A challenge of this kind may include a so-called Captcha and/or an image with numbers. The user inputs a corresponding response, which is transmitted back to the table control unit 6, and the safe operating mode is deactivated if the challenge is successful. In a second variant, on deactivation of the safe operating mode back to normal operating mode the procedure may be similar to that on triggering movement, in that when the operating element is actuated at the touch screen 12 the query signal is, for its part, transmitted to the table control unit 6, which waits for a deactivation period, which may correspond to the confirmation period, to see whether the second operating device 10 is actuated and both trigger signals are present, after which the safe operating mode is deactivated.

Finally, it should also be noted that activation of the safe operating mode is displayed by way of a display device 46 on the second operating device 10, for example by backlighting the operating button 18.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a magnetic resonance facility having a main magnet unit with a patient-receiving area, a movable, controllable patient table for positioning a patient in the patient-receiving area, a table control unit for controlling the patient table, and an operating facility on the main magnet unit for communicating with the table control unit, for operation of the patient table by a user, the method comprising:

setting control parameters, by a first, electronic operating device of the operating facility, for a movement of the patient table to be performed;

communicating, in a safe operating mode, the control parameters set from the first operating device to the table control unit over a first communication channel;

communicating, in the safe operating mode, a trigger signal suitable for triggering the movement defined by the control parameters, by a second, mechanical operating device of the operating facility, over each communication channel of two redundant second communication channels that are at least logically separated, to the table control unit;

separately processing, by the table control unit, the trigger signals received over the two redundant second communication channels; and triggering, by the second operating device, the movement of the patient table when there is a match between the trigger signals received over the two redundant second communication channels.

2. The method of claim 1, wherein the first operating device is a touch screen and/or the second operating device is a trigger button.

3. The method of claim 1, wherein each trigger signal of the two redundant second communication channels is generated by a switch associated with the respective communication channel, actuated mechanically by the second operating device, and/or the logical separation of the two redundant second communication channels is created at least by a use of two different communication protocols.

4. The method of claim 3, wherein the two different communication protocols are CANopen and CANsafe.

5. The method of claim 1, further comprising, after the table control unit has received the control parameters:

transmitting, by the table control unit, the control parameters back over the first communication channel and/or at least one further communication channel to the first operating device; and displaying, by a display of the first operating device, the transmitted control parameters.

6. The method of claim 5, wherein on detection of an actuation of the first operating device over the first communication channel, which confirms the transmitted control parameters, a confirmation signal is sent to the table control unit, wherein a presence of the confirmation signal is used as an additional condition for triggering the movement defined by the control parameters.

7. The method of claim 5, wherein the received control parameters undergo an error check at the operating facility and/or the table control unit, and
wherein, when an error is detected by the table control unit, an error signal is sent to the first operating device over the first communication channel and/or the at least one further communication channel.

8. The method of claim 1, wherein the first communication channel comprises at least one further processing facility, in which the control parameters are converted to a communication protocol suitable for the table control unit.

9. The method of claim 8, wherein the communication protocol is also used for the two redundant second communication channels and/or uses a same communication line to the table control unit.

10. The method of claim 1, wherein, for implementing continuous travel by continuously actuating the second operating device, the table control unit is constructed for stopping movement of the patient table unless both trigger signals are received within a predefined continuous period.

11. The method of claim 1, wherein the operating facility is constructed for sending the trigger signals when the second operating device is actuated within a confirmation period after the control parameters have been sent and/or, as an additional condition for triggering the movement, the table control unit monitors whether the match between the trigger signals has been received within a confirmation period after the control parameters have been received.

12. The method of claim 1, wherein, for generating the trigger signals in the second operating device and/or for a validity of the detection of the trigger signals received by the table control unit, a check is made of whether the actuation of the second operating device takes place for at least a purposefulness period.

13. The method of claim 1, wherein, for deactivating the safe operating mode and switching to a normal operating mode, a challenge-response method is used between the table control unit and the operating facility, or there is a check for actuation of the second operating device taking place within a confirmation period after deactivation has been selected by the first operating device.

14. The method of claim 13, wherein the patient table may be moved solely by way of the second operating device in the normal operating mode.

15. The method of claim 1, wherein activation and/or non-activation of the safe operating mode is displayed by a display of the operating facility, by backlighting the second operating device and/or by a mechanical switching of the second operating device.

16. A magnetic resonance facility comprising:
a main magnet unit with a patient-receiving area;
a movable, controllable patient table configured to position a patient in the patient-receiving area;
a control facility comprising a table control unit configured to control the patient table;
a communication facility; and
an operating facility on the main magnet unit configured to communicate with the table control unit by way of the communication facility, for operation of the patient table by a user,
wherein the operating facility has a first, electronic operating device configured to set control parameters for a movement of the patient table to be performed, and a second, mechanical operating device configured to trigger the movement, and
wherein the communication facility has a first communication channel for communicating control parameters that have been set to the table control unit in a safe operating mode and at least two redundant second communication channels that are at least logically separated, for communicating to the table control unit a respective trigger signal when the second operating device is actuated,
wherein the table control unit has two physically separated receiving units configured to receive the trigger signals, and
wherein operating facility is constructed for triggering a movement defined by the control parameters only when there is a match between the trigger signals received by the table control unit.

* * * * *